United States Patent [19]

Winkelmann

[11] 4,338,302
[45] Jul. 6, 1982

[54] HERBICOLIN AND MICROBIOLOGICAL METHOD FOR THE PREPARATION THEREOF

[76] Inventor: Gunther Winkelmann, Marchenseestr. 5, 7407 Rottenburg 4, Wendelsheim, Fed. Rep. of Germany

[21] Appl. No.: 189,638

[22] Filed: Sep. 22, 1980

[30] Foreign Application Priority Data

Sep. 26, 1979 [DE] Fed. Rep. of Germany ....... 2938993

[51] Int. Cl.³ .................. A61K 35/00; C12P 1/04; C12N 1/20
[52] U.S. Cl. .................. 424/117; 435/170; 435/253
[58] Field of Search .................. 435/170; 424/117

[56] References Cited
FOREIGN PATENT DOCUMENTS 2007734 of 0000 Fed. Rep. of Germany .
2443560 of 0000 Fed. Rep. of Germany .
2405265 5/1979 France .

OTHER PUBLICATIONS

ATCC Catalogue, 1978, pp. 308–310, 70, 71.
DSM Catalogue, 1977, No. 30,074.

*Primary Examiner*—Alvin E. Tanenholtz
*Assistant Examiner*—James Martinell
*Attorney, Agent, or Firm*—Birch, Stewart, Kolasch & Birch

[57] ABSTRACT

The antibiotic and antimycotic compound, herbicolin, is prepared from a strain of *Erwinia herbicola* by aerobic cultivation. Herbicolin consists of two chromatographically separable components, herbicolin A and herbicolin B. The compound of the invention has been characterized by IR spectra, solubility data, elemental analysis, characteristic reactions, UV absorption, detectable amino acids and fatty acids, C-13-NMR spectra and $R_f$ values. The herbicolins may be formulated into appropriate pharmaceutical preparations including pharmaceutically acceptable carriers or diluents.

15 Claims, 4 Drawing Figures

13C-NMR spectrum
Herbicolin A in 12CD3OD

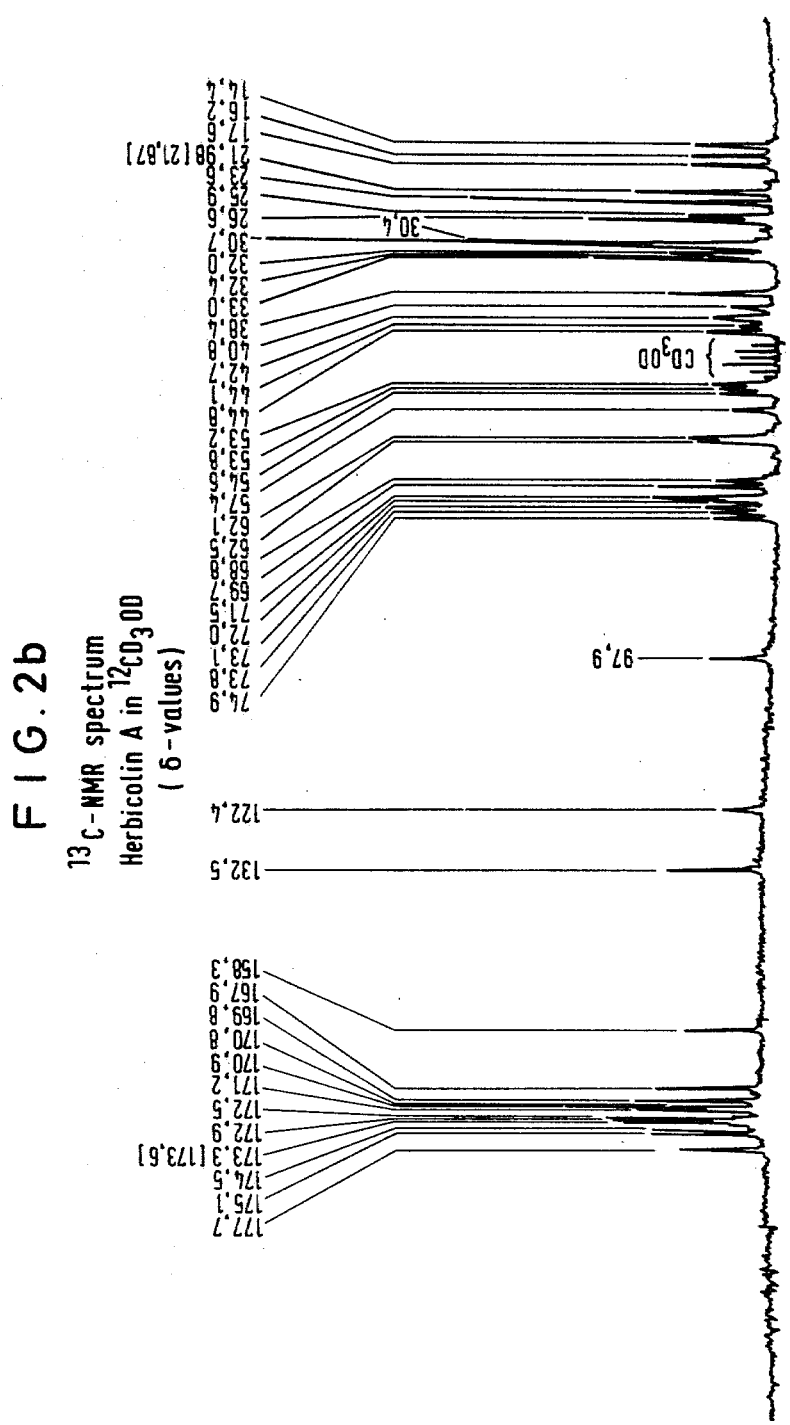

crystals of Herbicolin A
opto-electronic picture, maximum magnitude: 7200

HERBICOLIN AND MICROBIOLOGICAL METHOD FOR THE PREPARATION THEREOF

The present invention relates to a novel antibiotic and antimycotic, herbicolin, a microbiological method for its preparation from a strain of *Erwinia herbicola*, and pharmaceutical preparations containing this substance.

In medicine as well as in the plant protection field, there is still a need for highly effective antibacterially and antimycotically or antifungally active substances.

It has now been found that the novel antibiotic and antimycotic "herbicolin" can be obtained by aerobic cultivation of microorganisms of the order Eubacteriales, specifically the family Enterobacteriaceae, especially strains of the genus Erwinia, in an aqueous nutrient medium and subsequent isolation. The novel substance herbicolin consists of two chromatographically separable components, herbicolin A and herbicolin B, wherein herbicolin A is contained in herbicolin in a quantity of about 80% and herbicolin B in an amount of about 20%.

It has furthermore been found that the novel antibiotic herbicolin exhibits a strong antifungal effect against numerous fungi, while it is generally ineffective against bacteria.

Accordingly, the present invention is concerned with herbicolin, characterized in that it consists of herbicolin A and small amounts of herbicolin B, as well as with the preparation thereof.

Herbicolin A is characterized by the following parameters:

(1) characteristic IR bands in potassium bromide (FIG. 1) at 3200, 2900, 2830, 1730, 1650, 1530 cm$^{-1}$, (2) solubility:
very well soluble in:
  methanol,
  ethanol,
  1-propanol,
  1-butanol,
well soluble in:
  ethylene glycol,
  ethylene glycol monomethyl ether,
  glycerin,
  water.
sparingly soluble in:
  acetone,
  ethyl acetate,
  acetonitrile.
almost insoluble in:
  chloroform,
  dichloromethane,
  diethyl ether,
  petroleum ether.

The term "well soluble" is understood to mean that sufficient herbicolin A is present in solution to attain the biological effect.

(3) elementary analysis: found: C 46.1; H 7.1; N 11.8; S 1.9; molecular mass 1500–3000, (4) characteristic reactions:
  ninhydrin—negative
  chlorine/4,4'-tetramethyldiaminodiphenylmethane—positive, (5) no absorption in UV between 220 and 350 nm, (6) detectable amino acids:

| Amino Acids | Ratio (Approximation) |
|---|---|
| Glycine | 2 |
| L-Threonine | 1 |
| D-Allothreonine | 1 |
| D-Glutamic Acid | 1 |
| D-Leucine | 1 |
| L-Arginine | 1 |

(6a) detectable fatty acids:
  β-hydroxymyristic acid (7) C-13-NMR spectrum (FIGS. 2a and 2b) with ppm (δ) values in $^{12}CD_3OD$ of 177.7, 175.1, 174.5, 173.3 [173.6], 172.9, 172.5, 171.2, 170.9, 170.8, 169.8, 167.9, 158.3, 132.5, 122.4, 97.9, 74.9, 73.8, 73.1, 72.0, 71.5, 69.7, 68.8, 62.5, 61.2, 54.4, 54.6, 53.8, 53.2, 44.8, 44.1, 42.7, 40.8, 38.4, 33.0, 32.4, 32.0, 30.7, 30.4, 26.6, 25.9, 23.6, 21.98 [21.87], 17.6, 16.2, and 14.4, (8) the following $R_f$-values:
  1-butanol/glacial acetic acid/water (4:1:1) = $R_f$ 0.06
  chloroform/methanol/glacial acetic acid/water (65:25:3:4) = $R_f$ 0.10, (9) efficacy: strong fungitoxic effect at concentrations of 0.1 to 1 μg/ml;
  paramecia (slipper animalcules) and amoeba are killed in concentrations of 1–2 μg/ml in a few seconds;
  erythrocytes are lysed in concentrations of about 10 μg/ml (human blood).

In one of the aspects of the present invention, herbicolin is prepared by cultivating *Erwinia herbicola* (A 111) (DSM No. 1619) under aerobic conditions in an aqueous nutrient culture medium containing carbon sources and nitrogen sources, and obtaining the antibiotic from the resultant culture liquor.

The invention furthermore concerns a process for obtaining pure herbicolin A and pure herbicolin B. Further, the invention is directed to pharmaceutical compositions containing herbicolin, herbicolin A or herbicolin B.

Herbicolin, herbicolin A and herbicolin B are effective antibiotic and antimycotic agents. Herbicolin A and herbicolin B do not differ at all from each other with respect to their efficacy, or differ only slightly from each other in this respect.

Herbicolin A surpasses a number of known antifungal substances in effectiveness. The minimum inhibitory concentrations (MIC) thereof are of the order of 0.1–1.0 μg/ml. Herbicolin is effective against mycelium-forming and yeast-like fungi and can be utilized against phytophathogenic fungi as well as against dermatophytes. In addition, herbicolin is not difficulty degradable, so that no harm to the environment is to be expected from its use.

In accordance with this invention, herbicolin is produced by submerged culturing of suitable microorganisms in aqueous nutrient solutions under appropriate physical conditions. Herbicolin can be separated from the culture liquor by extraction or adsorption and can be concentrated by other suitable methods.

For obtaining herbicolin, the novel strain *Erwinia herbicola* (A 111) can be used from the order Eubacteriales, family Enterobacteriaceae, genus Erwinia. This strain was isolated in 1977 in Tuebingen, Germany from a surface pond and was deposited under number DSM 1619 on August 13, 1979 at the Deutsche Sammlung fuer Mikroorganismen (German Culture Collection) in Goettingen, West Germany. The strain was identified as *Erwinia herbicola* at the Bacteriological Institute of the South German Experimental and Research Establishment for Dairy Products and is characterized by the following properties:

(1) morphology: slender rods, length: 2.1–3.5 μm, vigorous motility; peritrichous flagella;

(2) biochemical characterization:
Gram-negative
oxidase— —
catalase—+
O/F test—fermentative growth with acid formation
Voges-Proskauer reaction—+
indole— —
$H_2S$— —
inositol—+
Phe-deaminase—+ (deamination of phenylalanine)
Orn (decarboxylase)— —
Lys (decarboxylase)— —
urease—+
arabinose—+/—
rhamnose— —
dextrose—+ (without gas)
gelatin liquefaction—+

The combined determinative features identify the strain (A 111) as pertaining to the species *Erwinia herbicola*.

Nutrient media containing the usual carbon and nitrogen sources and the necessary salts are utlized for the process of this invention to prepare herbicolin. The following can be used as carbon sources: carbohydrates, especially monosaccharides, such as, for example, glucose or fructose, but also disaccharides, such as, for example, maltose or saccharose. In addition, natural mixtures can be employed, e.g. yeast or malt extracts. Suitable nitrogen sources are assimilable nitrogen sources, such as corn steep liquor, soybean powder, peptone, meat extracts, yeast extracts, amino acids, such as, for example, asparagine, or inorganic compounds, such as, for example, ammonium sulfate or ammonium chloride.

Various inorganic salts are optionally employed, such as sodium chloride, potassium chloride, magnesium sulfate, potassium hydrogen phosphate, or potassium dihydrogen phosphate.

Auxiliary agents to be employed include defrothers or defoamers, such as polyols or silicones. To maintain a desired pH range, buffers can be utilized, for example, inorganic phosphates.

When conducting the process of this invention, the conditions used are aerobic, for example, using shaken cultures or aerated fermentor cultures. The percentage proportions of the ingredients in the nutrient solutions can vary within wide ranges; in general, the carbon sources constitute 1–10%, preferably 2–3%, the nitrogen sources 0.1–0.5%, preferably 0.2%. The salts are present in the usual concentrations, i.e., in the range between 0.01–1% by weight. Diluents for the nutrient media include deionized water or tap water.

Suitable conditions must be employed for sterilization, advantageously with smaller volumes for 20 minutes at 121° C., and with larger volumes for 30 minutes at 134° C. The pH values of the growing cultures are 5.5–8, preferably pH 7. The temperature of incubation can range between 4° and 30° C., preferably 22°–25° C.

The maximum of antibiotic production is determined with the aid of the plate diffusion test and *Neurospora crassa* as the test microorganism directly from the culture centrifugate.

In order to work up the herbicolin, the culture solution is freed of the bacteria by centrifuging. The centrifugate is passed through a "Servachrom-XAD" column (adsorbent on a polystyrene basis) and washed with 2–3 column volumes of deionized water. During this step, the herbicolin remains adsorbed on the column together with other lipophilic components. By subsequent elution with an acetone/water mixture (1:1) or solvent mixtures of a similar polarity, pigments and other slightly lipophilic components are removed.

By means of elution with pure methanol, ethanol, propanol, or other solvents of similar polarity, a solution of herbicolin is obtained with a few lipophilic accompanying substances and with only a slight yellow color remaining. In this case, a mixture of herbicolin A and herbicolin B is obtained in all instances. Preferably, methanol is employed as the eluting agent.

The thus-obtained solution, preferably a methanolic solution, can be conventionally concentrated by evaporation and/or freeze-dried. In this case herbicolin is produced consisting of about 80% herbicolin A and about 20% herbicolin B.

For additional purification and particularly for separating herbicolin into the two peptide antibiotics, herbicolin A and herbicolin B, the solution obtained during chromatography, preferably a methanolic solution, can be subjected to gel filtration on "Sephadex LH-20" using methanol or a solvent of similar polarity, such as ethanol or propanol as the eluting solvent, or to a separation on "Sephacryl 200" or on "Biogel P 4" in methanol/water (1:1) or acetone/water (1:1) or solvents of a similar polarity. During this gel filtration, the herbicolin is separated into herbicolin A and herbicolin B. The initial fractions obtained, which contain herbicolin A, are collected and evaporated in a conventional way or are lyophilized to yield a white fluffy material. Pure herbicolin A is thus obtained.

The fractions containing herbicolin B are likewise collected and evaporated or subjected to freeze-drying, thus providing pure herbicolin B.

Alternatively, the solution containing the herbicolin can be subjected to a Craig distribution on a Craig apparatus (e.g., "Boy 505" of Labortec) to separate the herbicolin into herbicolin A and herbicolin B. For example, mixtures of butanol/ethyl acetate/water (1:1:1) can be employed for the upper and lower phases for purposes of the Craig distribution. With a system containing 140 stages, herbicolin A is obtained in states 60–90.

The separation of herbicolin into herbicolin A and herbicolin B can likewise be accomplished by preparative thin-layer chromatography.

After removing the solvents in a conventional manner and/or after freeze-drying, the herbicolin, herbicolin A, or herbicolin B is obtained in a highly purified form as a white, amorphous powder. Herbicolin A can also be obtained in the crystalline form from concentrated methanolic solutions. The crystals obtained are fine needles having a length of about 10–50 μm with a predominantly rectangular cross-section.

Herbicolin, herbicolin A, and herbicolin B possess, as indicated above, essentially the same antibiotic and antimycotic effect.

The antibiotic herbicolin A of this invention is novel. It is characterized by the following data, to be taken in conjunction with the accompanying drawings wherein, FIG. 1 shows the infrared spectrum of herbicolin A;

FIG. 2a and 2b illustrate the NMR spectrum of herbicolin A; and

(a) Solubility and Properties:

Herbicolin A is a colorless compound showing high solubility in lower alcohols such as methanol, ethanol, 1-propanol, and 1-butanol. It is readily soluble in ethylene glycol, ethylene glycol monomethyl ether, glycerin, and water, wherein "readily soluble" is understood to mean that sufficient herbicolin A is present in solution to attain the biological effect.

In other solvents, such as acetone, chloroform, dichloromethane, acetonitrile, ethyl acetate, and petroleum ether, herbicolin A is almost insoluble. It shows a negative reaction with ninhydrin, but a positive reaction with chlorine/4,4′-tetramethyldiaminodiphenylmethane, indicating the absence of free amino groups and the presence of peptide bonds.

Figure 1:
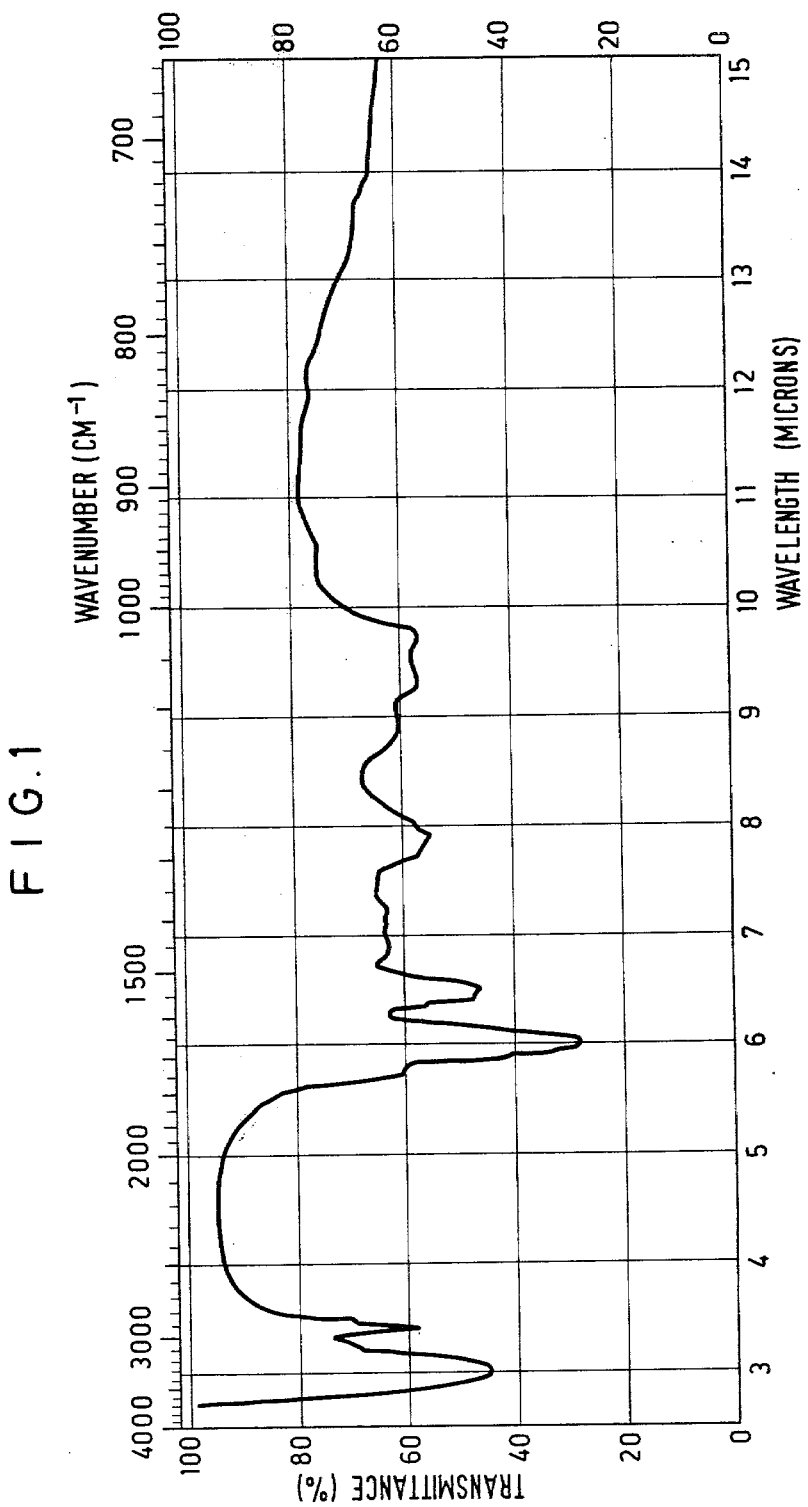

(b) The antibiotic shows no absorption in the UV spectrum between 220 and 350 nm. In the IR spectrum, bands occur at 3200, 2900, 2830, 1730, 1650, and 1530 $cm^{-1}$, showing pronounced amide I and amide II stretch bands at 1500–1700 $cm^{-1}$. FIG. 1 shows the IR spectrum thereof.

Figure 2A:
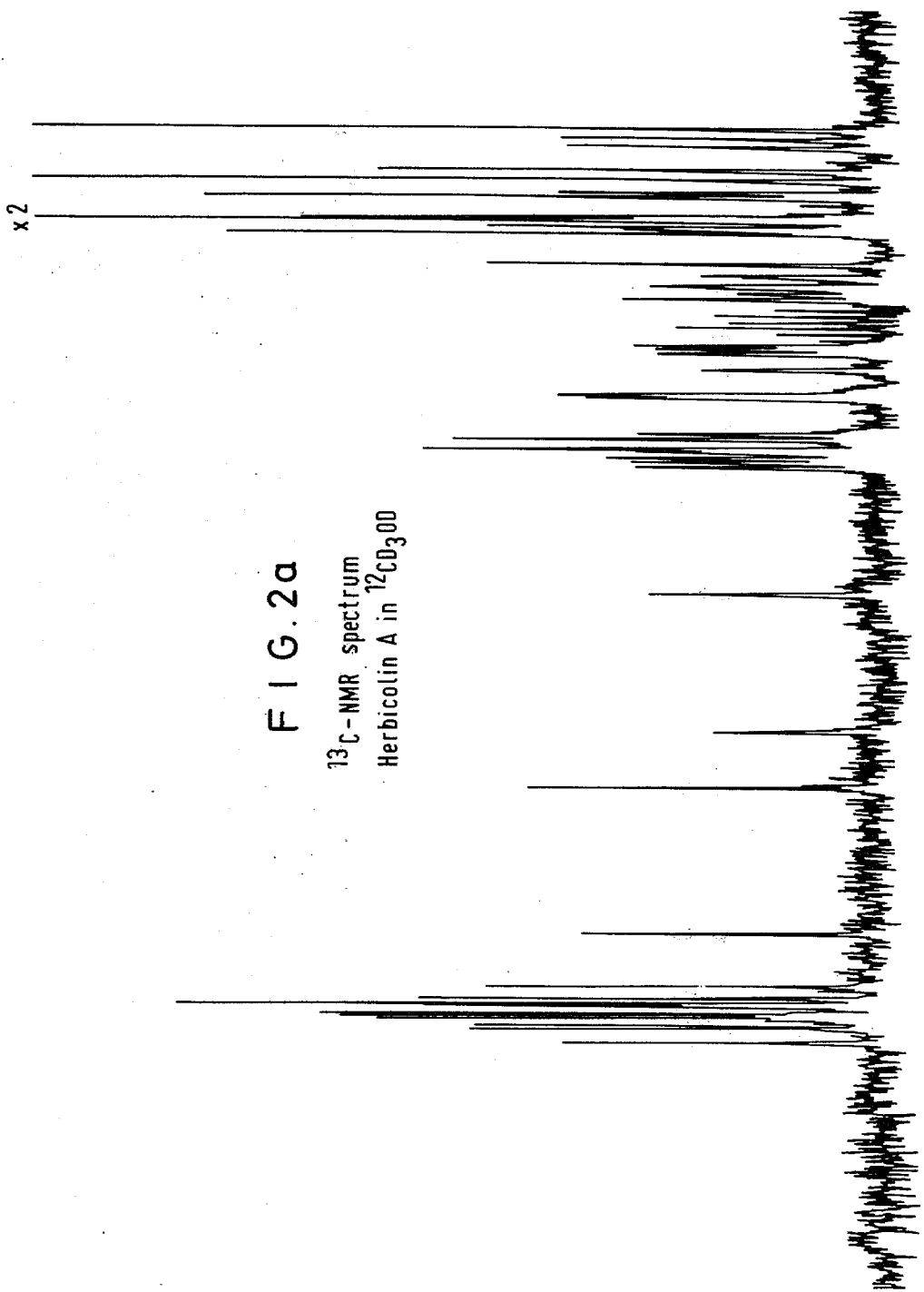

(c) Herbicolin A shows in $^{12}CD_3OD$ a characteristic —C-NMR spectrum. FIGS. 2a and 2b illustrate the NMR spectrum of herbicolin A.

(d) Amino acid analysis with the aid of an amino acid analyzer shows five amino acids, namely, glycine, threonine, leucine, glutamic acid, and arginine in a ratio of 2:2:1:1:1.

It can be assumed that the peptide residue of herbicolin A is a heptapeptide which can be cyclic or linear. An α-helix conformation of the peptide portion can be excluded by circular dichroism measurements.

(e) In thin-layer chromatography on silica gel plates, the antibiotic-producing substance forms two biologically active antibiotics, herbicolin A (about 80%) and herbicolin B (about 20%), which result in two spots thereon using as eluent 1-butanol/glacial acetic acid/water (4:1:1): herbicolin A ($R_f$=0.06) and herbicolin B ($R_f$=0.19). In the eluent chloroform/methanol/water (65:25:4), similar $R_f$-values are obtained. The herbicolins are made visible by treatment with chlorine/4,4′-tetramethyldiaminodiphenylmethane or by spraying with water.

(f) The usual sugars could not be detected. The non-peptide components probably are not carbohydrates. An aromatic or heteroaromatic residue of herbicolin A can likewise be excluded by the UV spectrum showing no absorption bands in the range from 220 to 320 nm.

Figure 3:
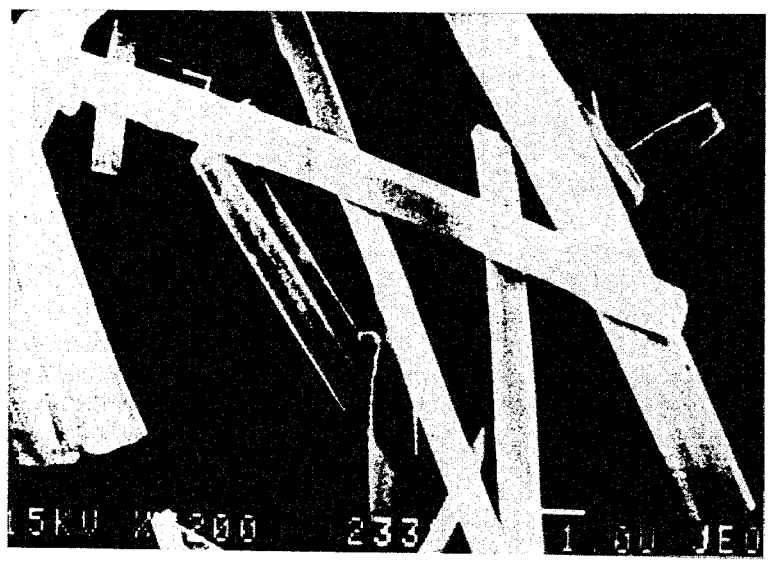
FIG. 3 is an optoelectronic photograph showing crystals of herbicolin A magnified 7200 times.

(g) As noted above, herbicolin A crystallizes from methanolic solutions in the form of fine needles having a length of about 10–50 μm and a predominantly rectangular cross-section. FIG. 3 illustrates crystals of herbicolin A in an optoelectronic photograph with a final magnification of 7200.

The complete structure of herbicolin A is still unknown.

The active agent of this invention, herbicolin, shows a strong fungitoxic effect at concentrations of 0.1–1 μg/ml and causes deformations of the tips of the hyphae. In addition, the active compound is effective against protozoa. Paramecium species (slipper animalcules) and amoebas are killed in a few seconds with concentrations of 1–2 μg/ml. Erythrocytes are lysed in concentrations of about 10 μg/ml (human blood). Green algae, such as, for example, Chlorella and Scenedesmus show very differing reactions. However, they are generally more resistant thereto.

All investigations regarding the site of activity point to the fact that herbicolin acts on the cytoplasmic membrane of eukaryotic organisms. In this connection, the individual groups of organisms show varying degrees of sensitivity.

The following examples are given merely as illustrative of the present invention and are not to be considered as limiting.

EXAMPLE 1

(a) Preparation of Herbicolin

To obtain herbicolin, a chemically defined medium is prepared containing, per liter, the following components: 7 g of $K_2HPO_4$, 3 g of $KH_2PO_4$, 0.5 g of trisodium citrate·$2H_2O$, 0.1 g of $MgSO_4·7H_2O$, 2 g of $(NH_4)_2SO_4$, and 20 g of glucose (autoclaved separately). The weighed materials are dissolved by means of distilled or deionized water to obtain the desired volume, adjusted to pH 6.8, and sterilized in an autoclave.

A 500-milliliter Erlenmeyer flask with lateral spout containing 100 ml of nutrient solution is inoculated with the producer strain Erwinia herbicola (A 111) and incubated for 24 hours at 22° C. on a rotating shaker at 120 r.p.m. By means of this subculture, a 5-liter Erlenmeyer flask with lateral spout and containing 2 liters of nutrient medium is inoculated and incubated for 48 hours at 22° C. at 110 r.p.m. Five additional 5-liter Erlenmeyer flasks with respectively 2 liters of nutrient solution are inoculated with this second subculture and incubated for three days at 22° C. and at 110 r.p.m.

The bacteria are separated by centrifuging (Sorvall, Rotor GSA) for 20 minutes at 6,000×g or by continuous separation (Sorvall, Rotor SZ-14 GK). The bacteria-free culture broth is passed over a "Servachrom-XAD-2" column (60×500 mm). The eluate is discarded. Thereafter, elution is carried out with five column volumes of deionized water to remove all water-soluble components which are not adsorbable. Herbicolin remains on the column together with other primarily lipophilic components. A portion of the accompanying lipophilic components as well as the largest portion of the yellow pigments can be removed by elution with acetone/water (1:1). The elution volume should not exceed one column volume, since minor amounts of herbicolin are concomitantly eluted even at this early stage.

Herbicolin is desorbed from the column with one column volume of pure methanol. The thus-obtained eluate is concentrated to a small volume on a forced circulation evaporator and introduced into a "Sephadex-LH-20" column (50×150 mm). By elution with pure methanol, the herbicolin fraction can be separated from other accompanying components.

Removal of the solvent and subsequent freeze-drying yield herbicolin as a white, amorphous powder.

(b) Preparation of Herbicolin A

To obtain herbicolin A, either the eluate of the XAD column or the further-purified fraction of the "Sephadex-LH-20" column is subjected to a Craig distribution. The upper phase and the lower phase are produced from butanol/ethyl acetate/water (1:1:1). The herbicolin fraction to be purified is dissolved in the upper phase. With a system of 140 stages, pure herbicolin A is obtained in stages 60-90. The fractions are concentrated to dryness and taken up on a small amount of methanol. Herbicolin A can be produced in the crystalline form from concentrated methanolic solutions.

EXAMPLE 2

Effect of Herbicolin A Against Neurospora crassa 74 A in the Plate Diffusion Test 100 ml of yeast/malt agar is produced for *Neurospora crassa*, this agar containing 1.5% agar, 0.4% yeast extract, 1% malt extract, and 0.4% glucose. After autoclaving, the mixture is allowed to cool to 45° C., and 0.1 ml of a spore solution (about $10^6$ spores/ml) is added thereto. After thorough distribution of the spores, the mixture is poured into sterile Petri dishes and allowed to cool. On filter plates having a diameter of 6 mm, 1 $\mu$l, 2 $\mu$l, 3 $\mu$l ... to 10 $\mu$l of a methanolic herbicolin solution (1 mg/ml) is applied. After drying in air for 15 minutes, these filter plates are placed on the nutrient substrate inoculated with fungal spores and incubated in an incubator at 27° C.

After 18 hours, depending on the amount of herbicolin utilized, differently large, growth-free zones are visible at concentrations of 1-5 $\mu$g and attain a diameter of 15-18 mm at 10 $\mu$g/plate.

EXAMPLE 3

Effect of Herbicolin A Against Neurospora crassa 74 A in Liquid Culture

Two liters of a chemically defined medium is prepared for *Neurospora crassa*, this medium containing the following components per liter of distilled water: 5 g of asparagine, 1 g of $K_2HPO_4.3H_2O$, 1 g of $MgSO_4.7H_2O$, 0.5 g of $CaCl_2.2H_2O$, 0.01 mg of $ZnSO_4.7H_2O$, and 2 g of glucose (autoclaved separately). After sterilization, the mixture is inoculated with $2 \times 10^6$ spores and distributed among 10 shaker flasks (200 ml each). Increasing increments (0, 0.1, 0.2, 0.3 ... to 1.0 ml) of a methanolic herbicolin A solution (0.1 mg/ml) are added thereto, and the flasks are incubated on a rotating shaker at 27° C.

After 48 hours each batch is subjected to filtration and the formed mycelium, after drying at 100° C. (24 hours), is determined by gravimetry.

As a typical result, the following data can be presented:

Control (without herbicolin A) 249.5 mg (=100% growth)

| Herbicolin A | Mycelium (Dry Weight) | % of Control |
|---|---|---|
| 0.1 ml | 204 mg | (96.2%) |
| 0.2 ml | 79 mg | (31.7%) |
| 0.3 ml | 26 mg | (10.4%) |
| 0.4 ml | 5 mg | (2.0%) |
| 0.5 ml | 2 mg | (1.0%) |
| 0.6-1 ml | 1 mg | |

The minimum inhibitory concentration thus is about 0.25 $\mu$g/ml.

EXAMPLE 4

Determination of the Spectrum of Activity of Herbicolin A

The fungi and bacteria to be tested are distributed with cell numbers of $10^6$ per 100 ml of nutrient agar in the form of spores or vegetative cells by pouring on plates or streaking on Petri dishes. Respectively, 10 $\mu$l of a methanolic herbicolin A solution is pipetted upon filter plates (diameter 6 mm) which, after drying in air, are placed on the Petri dishes with the various microorganisms. To test the fungi, yeast/malt agar is utilized, and Müller-Hinton agar is employed for testing the bacteria. A positive result (inhibition) is said to be present if inhibition zones larger than 9 mm become visible.

The thus-obtained spectrum of activity can be seen from Table I.

TABLE I

| Spectrum of Activity of Herbicolin A | |
|---|---|
| Aspergillus fumigatus | + |
| Aspergillus melleus | + |
| Botrytis cinerea | + |
| Fusarium dimerum | + |
| Gliocladium vermoeseni | + |
| Paecilomyces varioti | + |
| Neurospora crassa | + |
| Cryptococcus melibiosum | + |
| Candida guilliermondii | + |
| Candica albicans | + |
| Candida parapsilosis | + |
| Candida crusei | + |
| Schinzonella melanogramma | + |
| Urocystis occulta | + |
| Ustilago nuda | + |
| Trichophyton rubrum | + |
| Epidermophyton floccosum | + |
| Bacillus-subtilis | − |
| Enterobacter cloacae | − |
| Escherichia coli | − |
| Klebsiella pneumoniae | − |
| Mycoplasma laidlawii | − |
| Proteus mirabilis | − |
| Proteus vulgaris | − |
| Pseudomonas aeruginosa | − |
| Staphylococcus aureus | − |
| Staphylococcus epidermitis | − |
| Streptococcus pyogenes | − |

EXAMPLE 5

Comparison of the Antifungal Activity of Herbicolin A with Other Antifungal Agents (1) To demonstrate the effect of herbicolin A with other conventional antifungal substances, a comparative plate diffusion test is conducted with griseofulvin, amphotericin, and herbicolin A and with *Neurospora crassa* as the test microorganism. Respectively, 10 $\mu$g of the corresponding antibiotics is pipetted in the form of a methanolic solution on the filter plates and, after drying, placed on a nutrient substrate inoculated with *Neurospora crassa* spores. The following result is obtained: After an incubation of 18 hours at 27° C., no inhibition zone is found with griseofulvin; an inhibition zone of about 10 mm is found with amphotericin; and an inhibition zone of about 18 mm is observed with herbicolin A.

(2) In the same manner, various membrane-modifying peptide antibiotics are comparison-tested with herbicolin A:

Trichotoxin A 40, Suzukazillin, Alamethicin F 50, and herbicolin A, respectively, 10 $\mu$g/plate. The following result is obtained: Trichotoxin shows no inhibition zone at this concentration; Suzukazillin and Alamethicin show only a weak inhibition zone; whereas herbicolin A shows a clearly visible inhibition zone.

Herbicolin, herbicolin A and herbicolin B, prepared in accordance with the invention, may be formulated into antibiotic and/or antimycotic pharmaceutical compositions by conventional techniques well known in the field of pharmaceutical chemistry, utilizing an effective antibiotic or antimycotic amount of herbicolin, herbicolin A or herbicolin B and a pharmaceutically acceptable carrier or diluent. The compositions may be administered orally or by injection. Oral compositions can be administered in different forms such as dragees, tablets, gelatin capsules as well as other known forms and can be formulated in a manner well known to pharmaceutical chemists utilizing standard pharmaceutical excipients, carriers or diluents such as water, vegetable oils, syrup, gum arabic, gelatin, methylcellulose, polyglycols and others which may optionally be mixed with emulsifying agents. The herbicolins of the present invention may also be injected intramuscularly or endovenously in the form of an injectable solution. The pharmaceutical preparations can be liquid or dried, for example, lyophilized preparations, using suitable excipients or diluents which are well known to pharmaceutical chemists.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. Herbicolin A, characterized by the following properties:
   (1) characteristic IR bands in potassium bromide at 3200, 2900, 2830, 1730, 1650, 1530 cm$^{-1}$, as shown in the attached FIG. 1;
   (2) solubility:
      very well soluble in:
         methanol
         ethanol
         1-propanol
         1-butanol
      well soluble in:
         ethylene glycol
         ethylene glycol monomethyl ether
         glycerin
         water
      sparingly soluble in:
         acetone
         ethyl acetate
         acetonitrile
      almost insoluble in:
         chloroform
         dichloromethane
         diethyl ether
         petroleum ether
   wherein the term "well soluble" is understood to mean that sufficient herbicolin A is present in solution to attain the biological effect thereof;
   (3) elementary analysis: found: C 46.1; H 7.1; N 11.8; S 1.9; molecular mass 1500–3000;
   (4) characteristic reactions:
      ninhydrin—negative
      chlorine/4,4'-tetramethyldiaminodiphenylmethane—positive;
   (5) no absorption in the ultraviolet spectrum between 220 and 350 nm;
   (6) detectable amino acids:
   (6a) detectable fatty acids, $\beta$-hydroxy myritic acid

| Amino Acids | Ratio (Approximation) |
| --- | --- |
| Glycine | 2 |
| L-Threonine | 1 |
| D-Allothreonine | 1 |
| D-Glutamic Acid | 1 |
| D-Leucine | 1 |
| L-Arginine | 1 |

(7) $^{13}$C-NMR spectrum with ppm ($\delta$) values in $^{12}$CD$_3$OD of 177.7, 175.1, 174.5, 173.3, 172.9, 172.5, 171.2, 170.9, 170.8, 169.8, 167.9, 158.3, 132.5, 122.4, 97.9, 74.9, 73.8, 73.1, 72.0, 71.5, 69.7, 68.8, 62.5, 62.1, 57.4, 54.6, 53.8, 53.2, 44.8, 44.1, 42.7, 40.8, 38.4, 33.0, 32.4, 32.0, 30.7, 30.4, 26.6, 25.9, 23.6, 21.98, 17.6, 16.2, and 14.4, as shown in the attached FIGS. 2a and 2b;
   (8) the following R$_f$-values:
      1-butanol/glacial acetic acid/water (4:1:1) = R$_f$ 0.06
      chloroform/methanol/glacial acetic acid/water (65:25:3:4) = R$_f$ 0.10; and
   (9) efficacy: strong fungitoxic effect at concentrations of 0.1 to 1 $\mu$g/ml;
      paramecia species (slipper animalcules) and amoeba are killed in concentrations of 1–2 $\mu$g/ml in a few seconds; and
      erythrocytes are lysed in concentrations of about 10 $\mu$g/ml (human blood).

2. A process for the preparation of herbicolin which comprises cultivating a herbicolin-producing microorganism strain of *Erwinia herbicola* under aerobic conditions in an aqueous nutrient medium containing assimilable carbon sources and nitrogen sources, and isolating the herbicolin from the resultant culture liquor.

3. The process of claim 2, wherein the cultivation is conducted at a pH value of 5.5 to 8.

4. The process of claims 2 or 3, wherein the cultivation is conducted at a temperature of between 4° and 30° C.

5. The process of claim 2, wherein said microorganism is *Erwinia herbicola* (A 111) DMS 1619.

6. The process of claims 2, 3 or 5, wherein the reaction mixture is worked up by freeing the culture solution by centrifuging from the bacteria, introducing the centrifugate onto an adsorbent column, washing the mixture for the removal of pigments and other lipophilic components with a solvent, and then eluting the desired herbicolin with an alcoholic solvent.

7. The process of claim 6, wherein said alcoholic solvent is methanol.

8. The process of claim 7, wherein the thus-obtained eluate is evaporated to give herbicolin.

9. The process of claim 7, wherein the thus-obtained eluate is lyophilized.

10. The antibiotic and antimycotic substance herbicolin, which is prepared by a process comprising cultivating a herbicolin-producing microorganism strain of *Erwinia herbicola* under aerobic conditions in an aqueous nutrient medium containing assimilable carbon sources and nitrogen sources, and isolating the herbicolin from the resultant culture liquor.

11. Herbicolin in accordance with claim 10, which consists essentially of herbicolin A and small amounts of herbicolin B.

12. Herbicolin in accordance with claim 10, which consists essentially of 80% by weight of herbicolin A and 20% by weight of herbicolin B.

13. An antibiotic and antimycotic composition comprising an effective antibiotic or antimycotic amount of herbicolin in accordance with claim 10, and a pharmaceutically acceptable carrier or diluent.

14. An antibiotic and antimycotic composition in accordance with claim 13, wherein said herbicolin consists essentially of herbicolin A and small amounts of herbicolin B.

15. An antibiotic and antimycotic composition in accordance with claim 13, wherein said herbicolin consists essentially of 80% by weight of herbicolin A and 20% by weight of herbicolin B.

* * * * *